United States Patent
Bodhuri et al.

(10) Patent No.: US 10,800,787 B2
(45) Date of Patent: Oct. 13, 2020

(54) PROCESS FOR THE PREPARATION OF ACALABRUTINIB

(71) Applicant: Apotex Inc., Toronto (CA)

(72) Inventors: Prabhudas Bodhuri, San Ramon, CA (US); Boris Gorin, Oakville (CA); Melanie R. A. Green, Milton (CA); Gamini Weeratunga, Ancaster (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 16/605,972

(22) PCT Filed: Apr. 17, 2018

(86) PCT No.: PCT/CA2018/050459
§ 371 (c)(1),
(2) Date: Oct. 17, 2019

(87) PCT Pub. No.: WO2018/191815
PCT Pub. Date: Oct. 25, 2018

(65) Prior Publication Data
US 2020/0048264 A1 Feb. 13, 2020

Related U.S. Application Data

(60) Provisional application No. 62/487,683, filed on Apr. 20, 2017.

(51) Int. Cl.
C07D 487/04 (2006.01)
B01J 31/22 (2006.01)

(52) U.S. Cl.
CPC ........ *C07D 487/04* (2013.01); *B01J 31/2295* (2013.01)

(58) Field of Classification Search
CPC .................................................. C07D 487/04
USPC .......................................................... 544/350
See application file for complete search history.

(56) References Cited

U.S. PATENT DOCUMENTS

| 8,008,309 | B2 | 8/2011 | Honigberg et al. |
| 9,290,504 | B2 | 3/2016 | Bart et al. |
| 2017/0035881 | A1 | 2/2017 | Lannutti et al. |
| 2017/0239351 | A1 | 8/2017 | Hamdy et al. |
| 2018/0318297 | A1 | 11/2018 | Barf et al. |
| 2019/0367524 | A1 | 12/2019 | Cai et al. |

FOREIGN PATENT DOCUMENTS

| CN | 106588937 A | 4/2017 |
| CN | 107056786 A | 8/2017 |
| CN | 107522701 A | 12/2017 |
| CN | 108250186 A | 7/2018 |
| IN | 201641037734 A | 5/2018 |
| WO | 2013010868 A1 | 1/2013 |
| WO | 2016024231 A1 | 2/2016 |
| WO | 2017077507 A1 | 5/2017 |
| WO | 2019090269 A1 | 5/2019 |

OTHER PUBLICATIONS

Chan et al., "Kinetics of Amide Formation through Carbodiimide/N-Hydroxybenzotriazole (HOBt) Couplings", Journal of Organic Chemistry, 2007, pp. 8863-8869, vol. 72, No. 23.
Wuts et al., Greene's Protective Groups in Organic Synthesis, 2007, 27 pages, Fourth Edition, John Wiley & Sons, Inc., Hoboken, USA.

*Primary Examiner* — Douglas M Willis
(74) *Attorney, Agent, or Firm* — The Webb Law Firm

(57) ABSTRACT

The present invention provides processes for the preparation of Acalabrutinib (1), as well as intermediates useful in the preparation thereof. In particular, processes are provided for coupling of a compound of Formula (5) and 2-butynoic acid in the presence of Carbodiimide (8) to afford Acalabrutinib (1).

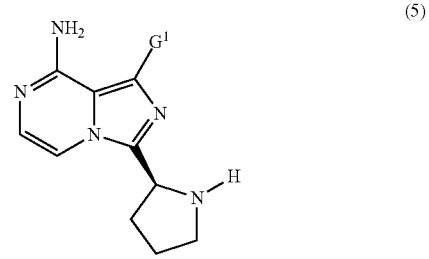

(5)

10 Claims, No Drawings

PROCESS FOR THE PREPARATION OF ACALABRUTINIB

CROSS-REFERENCE TO RELATED APPLICATIONS

This application is the United States national phase of International Application No. PCT/CA2018/050459 filed Apr. 17, 2018, and claims priority to U.S. Provisional Patent Application No. 62/487,683 filed Apr. 20, 2017, the disclosures of which are hereby incorporated by reference in their entirety.

BACKGROUND OF THE INVENTION

Field of the Invention

The present invention relates to processes for the preparation of Acalabrutinib (1) and intermediates used in the preparation thereof.

Description of Related Art

Acalabrutinib (1), or 4-{8-amino-3-[(2S)-1-(but-2-ynoyl)pyrrolidin-2-yl]imidazo[1,5-a]pyrazin-1-yl}-N-(pyridin-2-yl)benzamide, exhibits activity as a Bruton's tyrosine kinase (BTK) inhibitor and is undergoing evaluation in clinical trials in patients with chronic lymphocytic leukemia (CLL)/small lymphocytic lymphoma (SLL) in Europe and the United States. Acalabrutinib (1) has the following structural formula:

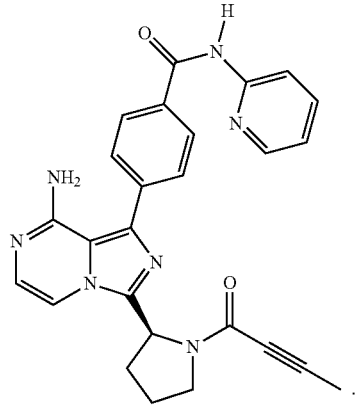

(1)

Scheme 1 depicts a method of preparing Acalabrutinib (1) that is described in WO 2013/010868 A1. In this method, Acalabrutinib (1) is prepared from bromide (A) by Suzuki coupling with boronic acid (B), followed by deprotection of the pyrrolidine amine of intermediate (C) to provide intermediate (D), and a coupling with 2-butynoic acid (E) to yield Acalabrutinib (1).

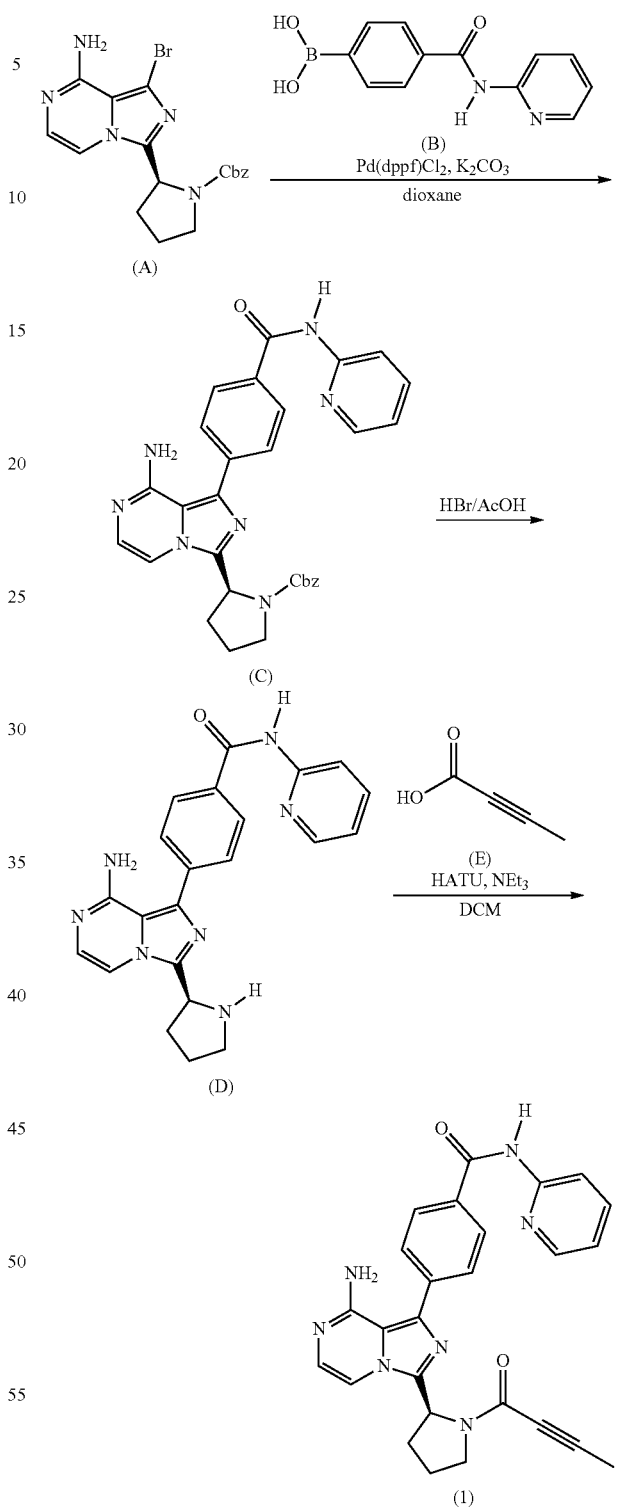

Scheme 1 (Prior Art)

However, the process described in WO 2013/010868 A1 suffers from a number of limitations that reduce its usefulness for large scale manufacturing. For example, the coupling between compounds (A) and (B) is induced by microwave irradiation at 140° C., which is not feasible for conventional reactor-type industrial production. Further-more, the yield from compound (A) to Acalabrutinib (1) is low at only 8%, largely owing to the poor yield (18%) achieved for the final coupling step between compound (D) and 2-butynoic acid (E), which is facilitated by coupling reagent 1-[bis(dimethylamino)methylene]-1H-1,2,3-triazolo[4,5-b]pyridinium 3-oxide hexafluorophosphate (HATU).

Accordingly, a need exists for improved processes for the preparation of Acalabrutinib (1), and the intermediates used in such preparations, that are more amenable to scale-up and use on a commercial scale.

BRIEF SUMMARY OF THE INVENTION

The present invention provides improved processes for the preparation of Acalabrutinib (1), as well as new intermediates and processes for their preparation.

As shown in Scheme 2, Acalabrutinib (1) may be prepared by coupling a compound of Formula (5) with an activated acid derivative, prepared by treatment of 2-butynoic acid of Formula (7) with Carbodiimide (8) and, optionally, Additive (A-H). As part of the processes of the present invention, conditions are provided for this coupling that provide good yields of either Acalabrutinib (1), or the novel intermediate compound of Formula (2), which can be further reacted to provide Acalabrutinib (1). Preferred embodiments of the invention utilize cost-effective, readily available reagents and produce easily removable by-products, thereby providing significant advantages for large scale industrial manufacturing. Other embodiments of the processes of the invention provide an alternative to the use of microwave radiation to facilitate the Suzuki coupling reaction (for example, depending on the nature of the substituent $G^1$, in the preparation of the compound of Formula (5), or in the conversion of the compound of Formula (2) to Acalabrutinib (1) in Scheme 2).

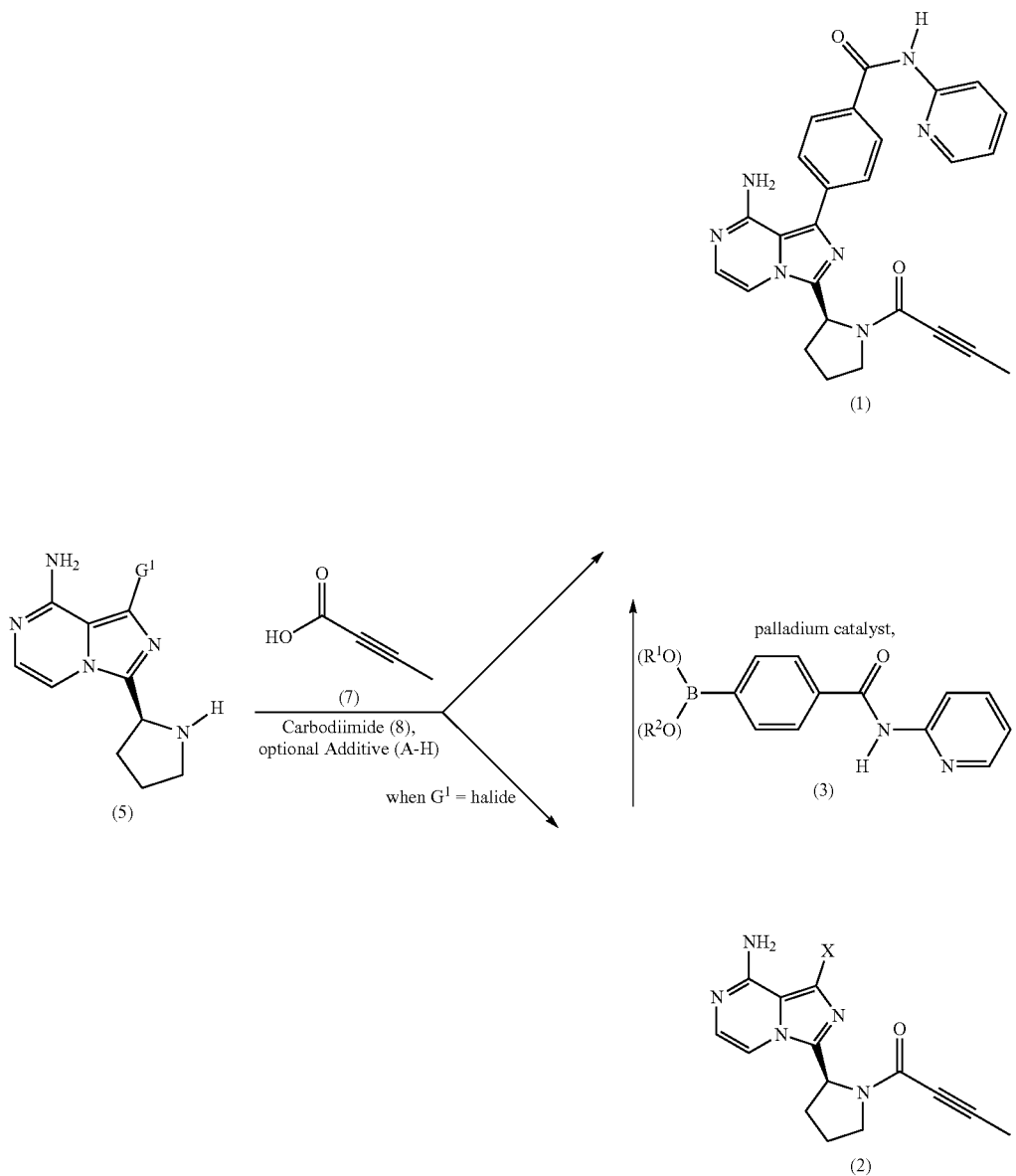

wherein
G¹ is halide or

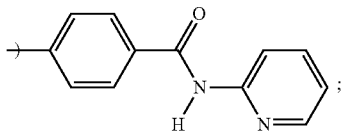 [SMILES: Cc1ccc(C(=O)Nc2ccccn2)cc1]
;

Carbodiimide (8) is a suitable carbodiimide capable of facilitating amide formation between a carboxylic acid and an amine;

A in Additive (A-H) is selected from the group consisting of:

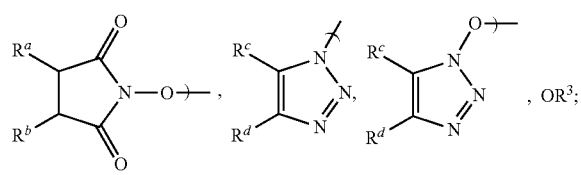, OR³;

$R^a$ and $R^b$ are either (a) hydrogen or (b) $R^c$ and $R^d$;

$R^c$ and $R^d$, taken together with the carbon atoms to which they are bonded form a ring selected from the group consisting of an aryl group having 6 to 10 ring carbon atoms, a substituted aryl group having 6 to 10 ring carbon atoms, a heteroaryl group having 5 to 9 carbon atoms and at least one heteroatom selected from S, N and O, a substituted heteroaryl group having 5 to 9 carbon atoms and at least one heteroatom selected from S, N and O, an aliphatic group having 1 to 10 carbon atoms and a substituted aliphatic group having 1 to 10 carbon atoms; and $R^3$ is selected from the group consisting of an aryl group having 6 to 10 ring carbon atoms and a substituted aryl group having 6 to 10 ring carbon atoms;

X is halide; and $R^1$ and $R^2$ are either (a) two independent groups selected from the group consisting of H and alkyl; or (b) $R^1$ and $R^2$ together form a substituted or unsubstituted heterocyclic ring with the boron and oxygen atoms to which they are bonded.

Accordingly, in a first aspect of the present invention, there is provided a process for the preparation of a compound of Formula (1) or a salt thereof, comprising:

(i) coupling a compound of Formula (5):

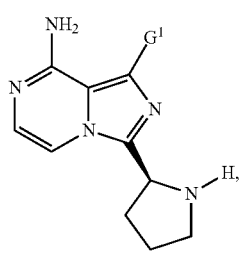

(5)

with an activated acid derivative, prepared by treatment of a compound of Formula (7):

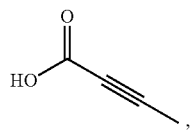

(7)

with Carbodiimide (8),
wherein
G¹ is halide or

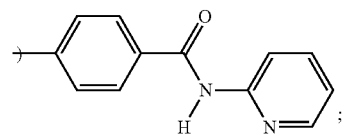
;

and
Carbodiimide (8) is a suitable carbodiimide capable of facilitating amide formation between a carboxylic acid and an amine;

to provide either Acalabrutinib (1) when G¹ is

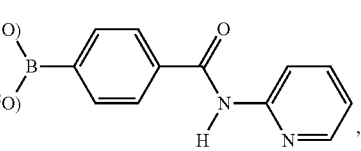

or, when G¹ is halide, a compound of Formula (2):

(2)

wherein
X is halide; and (ii) when G¹ is halide, coupling, in the presence of a palladium catalyst, a base (B1) and a solvent (S2), the compound of Formula (2) with a compound of Formula (3):

(3)

wherein
$R^1$ and $R^2$ are either (a) two independent groups selected from the group consisting of H and alkyl; or (b) $R^1$ and $R^2$ together form a substituted or unsubstituted heterocyclic ring with the boron and oxygen atoms to which they are bonded.

In one preferred embodiment of the first aspect, Carbodiimide (8) is selected from the group consisting of N,N'-dicyclohexylcarbodiimide, N,N'-diisopropylcarbodiimide, N-(3-dimethylaminopropyl)-N'-ethylcarbodiimide and N-(3-dimethylaminopropyl)-N'-ethylcarbodiimide hydrochloride. More preferably, Carbodiimide (8) is N,N'-dicyclohexylcarbodiimide or N-(3-dimethylaminopropyl)-N'-ethylcarbodiimide hydrochloride.

In a second preferred embodiment of the first aspect, Carbodiimide (8) is used in combination with Additive (A-H) wherein A is selected from the group consisting of:

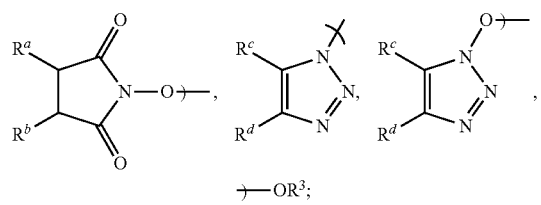

wherein

R$^a$ and R$^b$ are either (a) hydrogen or (b) R$^c$ and R$^d$;

R$^c$ and R$^d$, taken together with the carbon atoms to which they are bonded form a ring selected from the group consisting of an aryl group having 6 to 10 ring carbon atoms, a substituted aryl group having 6 to 10 ring carbon atoms, a heteroaryl group having 5 to 9 carbon atoms and at least one heteroatom selected from S, N and O, a substituted heteroaryl group having 5 to 9 carbon atoms and at least one heteroatom selected from S, N and O, an aliphatic group having 1 to 10 carbon atoms and a substituted aliphatic group having 1 to 10 carbon atoms; and R$^3$ is selected from the group consisting of an aryl group having 6 to 10 ring carbon atoms and a substituted aryl group having 6 to 10 ring carbon atoms.

Preferably, for Additive (A-H), R$^c$ and R$^d$ taken together with the carbon atoms to which they are bonded form a ring selected from the group consisting of phenyl and substituted phenyl and R$^3$ is selected from the group consisting of phenyl and substituted phenyl. More preferably, Additive (A-H) is selected from the group consisting of N-hydroxysuccinimide, 1-hydroxy-1H-benzotriazole, N-hydroxyphthalimide, benzotriazole and 4-nitrophenol.

In the second preferred embodiment of the first aspect, the activated acid derivative of the compound of Formula (7) is preferably pre-formed prior to contact with the compound of Formula (5).

Within the second preferred embodiment of the first aspect, the activated acid derivative is a compound of Formula (4):

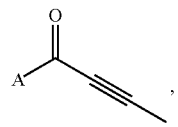

(4)

wherein

A is selected from the group consisting of:

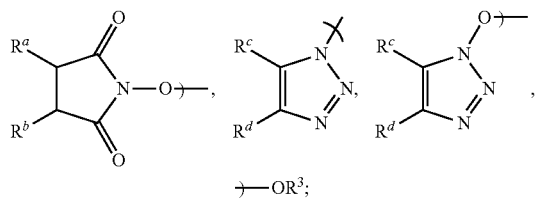

wherein

R$^a$ and R$^b$ are either (a) hydrogen or (b) R$^c$ and R$^d$;

R$^c$ and R$^d$, taken together with the carbon atoms to which they are bonded form a ring selected from the group consisting of an aryl group having 6 to 10 ring carbon atoms, a substituted aryl group having 6 to 10 ring carbon atoms, a heteroaryl group having 5 to 9 carbon atoms and at least one heteroatom selected from S, N and O, a substituted heteroaryl group having 5 to 9 carbon atoms and at least one heteroatom selected from S, N and O, an aliphatic group having 1 to 10 carbon atoms and a substituted aliphatic group having 1 to 10 carbon atoms; and R$^3$ is selected from the group consisting of an aryl group having 6 to 10 ring carbon atoms and a substituted aryl group having 6 to 10 ring carbon atoms.

Preferably, A is selected from the group consisting of:

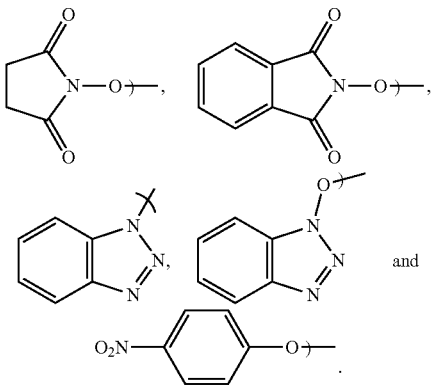

and

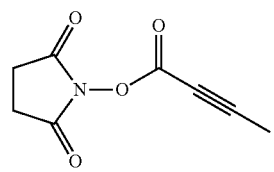

More preferably, the compound of Formula (4) is a compound of Formula (4-A):

(4-A)

Within the second preferred embodiment of the first aspect, it is preferred that the compound of Formula (4) is isolated prior to coupling with a compound of Formula (5).

In a third preferred embodiment of the first aspect, G¹ is

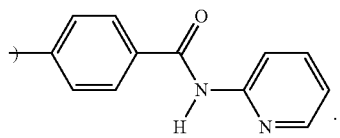 [SMILES: Cc1ccc(C(=O)Nc2ccccn2)cc1]

In a fourth preferred embodiment of the first aspect, G¹ is halide.

In a fifth preferred embodiment of the first aspect, the palladium catalyst used in step (ii) is 1,1'-bis(diphenylphosphino)ferrocene]dichloropalladium.

In a sixth preferred embodiment of the first aspect, R¹ and R² in the compound of Formula (3) are both H or R¹ and R² together form

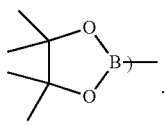

In a second aspect of the present invention, there is provided a compound of Formula (5-B):

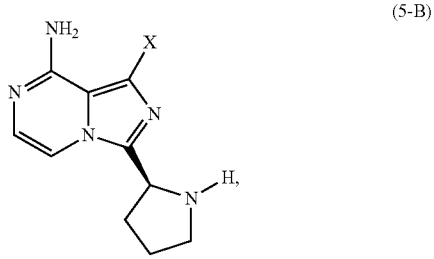

(5-B)

wherein

X is halide.

In a preferred embodiment of the second aspect, X is bromide.

In a third aspect of the present invention, there is provided a compound of Formula (2):

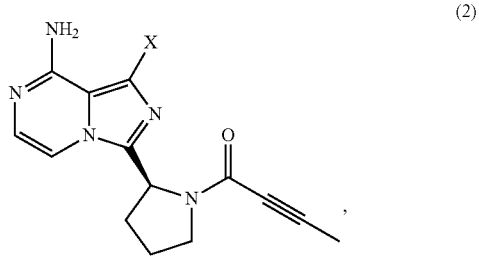

(2)

wherein

X is halide.

In a preferred embodiment of the third aspect, X is bromide.

DETAILED DESCRIPTION OF THE INVENTION

Development of the processes of the present invention followed from the discovery by the inventors that problems associated with the known processes for the preparation of Acalabrutinib (1) could be addressed through the use of novel activation and coupling conditions between a compound of Formula (5) and 2-butynoic acid (7). Additionally, when G¹ is halide, a novel pathway to Acalabrutinib (1), proceeding through the compounds of Formulas (5-B) and (2) is provided. In both the direct and indirect pathways to Acalabrutinib (1), embodiments of the invention provide processes for the coupling of the compound of Formula (5) and 2-butynoic acid (7) in good yields.

As used herein, the term "aliphatic", alone or as part of another substituent, means, unless otherwise stated, a straight chain, branched chain or cyclic hydrocarbon radical, or a combination thereof, which may be fully saturated, or mono- or polyunsaturated, and can include di- and multivalent radicals, having the number of carbon atoms designated. Examples of saturated hydrocarbon radicals include, but are not limited to, groups such as methyl, ethyl, n-propyl, iso-propyl, n-butyl, t-butyl, iso-butyl, sec-butyl, hexanyl, 2-methyl-2-hexanyl, cyclohexyl, 1-methylcyclohexyl, cyclopropylmethyl, and isomers of, for example, n-pentyl, n-hexyl, n-heptyl, n-octyl, and the like. An unsaturated hydrocarbon radical is one having one or more double bonds or triple bonds. Examples of unsaturated hydrocarbon radicals include, but are not limited to, vinyl, 2-propenyl, crotyl, 2-isopentenyl, 2-(butadienyl), 2,4-pentadienyl, 3-(1,4-pentadienyl), norbornenyl, ethynyl, 1-propynyl, 2-propynyl, 3-butynyl, and the higher homologs and isomers.

As used herein, the term "alkyl", alone or as part of another substituent, means, unless otherwise stated, a straight or branched chain, saturated hydrocarbon radical having the number of carbon atoms designated (e.g., C1-C4 means one to four carbon atoms). When there is no indication of the number of carbon atoms in the alkyl, it is meant, unless otherwise indicated by context, that there are from 1 to 10 carbons. Examples of saturated hydrocarbon groups include methyl, ethyl, n-propyl, iso-propyl, n-butyl, t-butyl, iso-butyl and sec-butyl.

As used herein, the term "aryl", alone or as part of another substituent, means, unless otherwise stated, a polyunsaturated, aromatic, hydrocarbon radical which can be a single ring or multiple rings (preferably from 1 to 3 rings) which are fused together or linked covalently having the number of carbon atoms designated. When there is no indication of the number of carbon atoms in the aryl, it is meant, unless otherwise indicated by context, that there are from 6 to 18 carbons. Non-limiting examples of aryl groups include: phenyl, 1-naphthyl, 2-naphthyl and 4-biphenyl.

As used herein, the term "arylalkyl", alone or as part of another substituent, means, unless otherwise stated, an aryl substituent as defined herein attached through an alkyl radical to the parent structure. When there is no indication of the number of carbon atoms in the arylalkyl group, it is meant, unless otherwise indicated by context, that there are from 7 to 20 carbons. Non-limiting examples of arylalkyl groups include benzyl, and phenethyl.

As used herein, the term "substituted" refers to the replacement of one or more hydrogen atoms with any one of a variety of substituents. A substituent may be a non-hydrogen atom or multiple atoms of which at least one is a non-hydrogen atom and one or more may or may not be hydrogen atoms. A substituted group (e.g., substituted —CH₂CH₃) may be fully substituted (e.g., —CF₂CF₃), mono-substituted (e.g., —CH₂CH₂F) or substituted at a level anywhere in-between fully substituted and mono-substituted (e.g., —CH₂CHF₂, —CH₂CF₃, —CF₂CH₃, —CFHCHF₂, etc.). Substituted compounds may comprise substituents selected from the group consisting of: R'", OR", NR"R", SR", halogen, SiR'"R'"R'", OCOR'", COR", CO₂R", CONR"R", NR"CO₂R'", NR"COR'", SOR'", SO₂R'", ON, NO₂ and CF₃. As used herein, each R" may be selected, independently, from the group consisting of hydrogen, an aliphatic group, aryl and arylalkyl. As used herein, each R'" may be selected, independently, from the group consisting of an aliphatic group, aryl and arylalkyl. Examples of substituent groups on substituted aryl and heteroaryl groups include nitro, halide and trifluoromethyl. Examples of substituent groups on substituted heterocyclic groups include alkyl.

As used herein, the term "heterocyclic", alone or as part of another substituent, means, unless otherwise stated, a saturated or unsaturated cyclic radical which can be a single ring or multiple rings (preferably from 1 to 3 rings) which are fused together or linked covalently having the number of carbon atoms designated and having as ring members atoms of at least two different elements. When there is no indication of the number of carbon atoms in the heterocycle, it is meant, unless otherwise indicated by context, that there are from 4 to 20 carbons. Non-limiting examples include 4,4,5,5-tetramethyl-1,3,2-dioxaborolanyl (pinacolborane) and 1,3,2-benzodioxaborole (catecholborane).

As used herein, the term "heteroaryl" alone or as part of another substituent, means, unless otherwise stated, an aryl group that contains from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridinyl and isoquinolyl.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

As used herein, the terms "wt %" or "% w/w" refer to weight percent and is used to express weight solute/weight solution as a percentage.

As used herein, the term "volumes" refers to the parts of solvent or liquids by volume (mL) with respect to the weight of solute (g). For example, when a reaction is conducted using 1 g of starting material and 100 mL of solvent, it is said that 100 volumes of solvent are used.

As used herein, "room temperature" generally refers to a temperature of 20-25° C.

As used herein, the term "about" means "close to" and that variation from the exact value that follows the term is within amounts that a person of skill in the art would understand to be reasonable. For example, when the term "about" is used with respect to temperature, a variation of ±5° C. is generally acceptable when carrying out the processes of the present invention; when used with respect to mole equivalents, a variation of ±0.1 moles is generally acceptable; and when used with respect to volumes, a variation of 10% is generally acceptable.

In one embodiment of the present invention, a process is provided for the preparation of Acalabrutinib (1) or a salt thereof, comprising:

(i) coupling, in the presence of a solvent (S1), a compound of Formula (5):

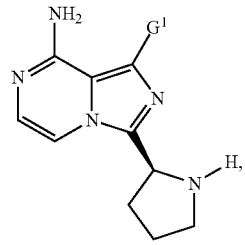

with an activated acid derivative, prepared by treatment of a compound of Formula (7):

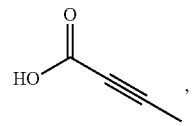

with Carbodiimide (8),
wherein
G¹ is halide or

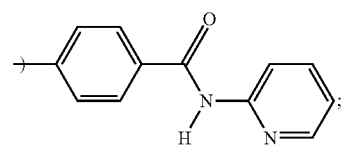

to provide either Acalabrutinib (1) or, when G¹ is halide, a compound of Formula (2):

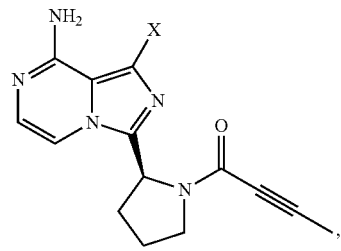

wherein
X is halide; and
(ii) when G¹ is halide, coupling, in the presence of a palladium catalyst, a base (B1) and a solvent (S2) of the compound of Formula (2) with a compound of Formula (3):

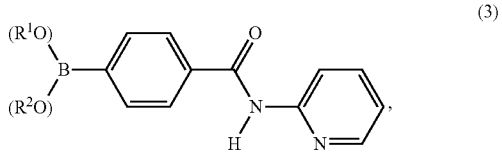

(3)

wherein
R¹ and R² are either (a) two independent groups selected from the group consisting of H and alkyl; or (b) R¹ and R² together form a heterocyclic ring with the boron and oxygen atoms to which they are bonded.

Carbodiimide (8) may be any suitable carbodiimide capable of facilitating amide formation between a carboxylic acid and an amine. Preferably, Carbodiimide (8) is selected from the group consisting of N,N'-dicyclohexylcarbodiimide (DCC), N,N'-diisopropylcarbodiimide (DIC), N-(3-dimethylaminopropyl)-N'-ethylcarbodiimide (EDC), and N-(3-dimethylaminopropyl)-N'-ethylcarbodiimide hydrochloride (EDC.HCl). Most preferably, the Carbodiimide (8) is DCC or EDC.HCl.

Carbodiimide (8) may be used exclusively to activate the compound of Formula (7) or it may be used in combination with Additive (A-H).

Additive (A-H) is selected from the group consisting of:

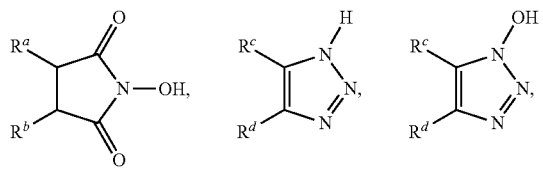

$R^3$—OH and salts thereof;
wherein
$R^a$ and $R^b$ are either (a) hydrogen or (b) $R^c$ and $R^d$; and
$R^c$ and $R^d$, taken together with the carbon atoms to which they are bonded form a ring selected from the group consisting of an aryl group having 6 to 10 ring carbon atoms, a substituted aryl group having 6 to 10 ring carbon atoms, a heteroaryl group having 5 to 9 carbon atoms and at least one heteroatom selected from S, N and O, a substituted heteroaryl group having 5 to 9 carbon atoms and at least one heteroatom selected from S, N and O, an aliphatic group having 1 to 10 carbon atoms and a substituted aliphatic group having 1 to 10 carbon atoms.

When $R^c$ and $R^d$ form a ring, the ring is fused with the imide or triazole ring. Preferably, when $R^c$ and $R^d$ form an aryl group, the aryl group is selected from the group consisting of phenyl, 1-naphthyl, 2-naphthyl and 4-biphenyl. More preferably, when $R^c$ and $R^d$ form an aryl group, the aryl group is phenyl. Preferably, when $R^c$ and $R^d$ form a heteroaryl group, the heteroaryl group is selected from the group consisting of pyridinyl and isoquinolyl. Preferably, when $R^c$ and $R^d$ form a substituted aryl or heteroaryl group, the substituents are selected from the group consisting of halide, nitro and trifluoromethyl. Preferably, when $R^c$ and $R^d$ form an aliphatic group, the aliphatic group is norbornenyl. Preferably, when $R^c$ and $R^d$ form a substituted aliphatic group, the substituted aliphatic group is 7-oxanorbornenyl. Most preferably, $R^c$ and $R^d$ form a phenyl ring.

$R^3$ is selected from the group consisting of an aryl group having 6 to 10 ring carbon atoms and a substituted aryl group having 6 to 10 ring carbon atoms. Preferably, when $R^3$ is an aryl group, the aryl group is selected from the group consisting of phenyl, 1-naphthyl, 2-naphthyl and 4-biphenyl. When $R^3$ is a substituted aryl group, the substituents are selected from the group consisting of halide, nitro and trifluoromethyl. Preferably, the substituents are selected from the group consisting of fluoro, chloro and nitro. Most preferably, $R^3$ is 4-nitrophenyl.

Preferably, Additive (A-H) is selected from the group consisting of N-hydroxysuccinimide (HOSu), 1-hydroxy-1H-benzotriazole (HOBt), N-hydroxyphthalimide, benzotriazole and 4-nitrophenol. Most preferably, Additive (A-H) is N-hydroxysuccinimide.

When Carbodiimide (8) is used exclusively (additive (A-H) is not used), a preferred approach is a 'one-pot' approach wherein treatment of the compound of Formula (7) with Carbodiimide (8) to provide an activated acid derivative is conducted in the presence of the compound of Formula (5). Alternatively, particularly when Additive (A-H) is used, the activation of the compound of Formula (7) may be conducted in a separate reaction step using a 'step-wise' approach to afford a pre-formed activated acid derivative prior to contact with a compound of Formula (5). In the latter case, the pre-formed derivative may or may not be isolated prior to coupling.

When the activation and coupling steps are separated, similar conditions may be employed for both reactions. For example, similar solvents and reaction temperatures are suitable for both steps, although optimal conditions for each step may differ. In the step-wise approach, treatment of the compound of Formula (7) with Carbodiimide (8) and Additive (A-H) is preferably conducted in the presence of a solvent selected from the group consisting of halogenated hydrocarbons and alkyl esters, whereas the preferred solvent (S1) for the coupling reaction is a halogenated hydrocarbon.

When Additive (A-H) is used, the activated acid derivative is believed to be a compound of Formula (4):

(4)

wherein A is as defined above. Preferably, A in Additive (A-H) is selected from the group consisting of:

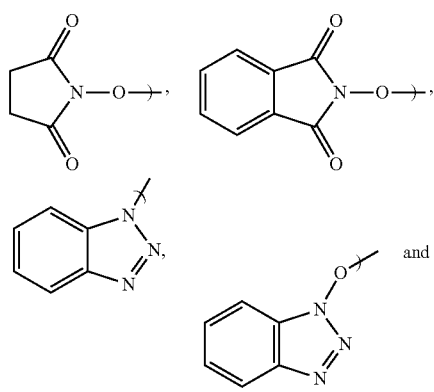

and

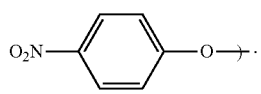

Most preferably, the compound of Formula (4) is a compound of Formula (4-A):

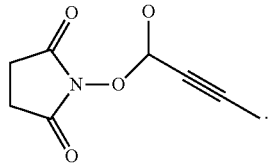

(4-A)

The coupling of the compound of Formula (5) and the activated acid derivative is conducted in the presence of a solvent (S1). Solvent (S1) is preferably selected from the group consisting of halogenated hydrocarbons, alkyl esters, ethers, nitriles and formamides. Preferably, solvent (S1) is selected from halogenated hydrocarbons and alkyl esters. More preferably, solvent (S1) is ethyl acetate or dichloromethane. Most preferably, solvent (S1) is dichloromethane.

The coupling of the compound of Formula (5) and the activated acid derivative may be conducted at any suitable temperature between about −15° C. and the boiling point of the solvent. Preferably, the temperature is in the range of about −15° C. to about 20° C., more preferably between about −5° C. and about 5° C.

As illustrated in the following examples, use of step (i) in the preparation of Acalabrutinib (1) provides an increase in yield when compared to the corresponding reaction in WO 2013/010868. For example, in the following examples, yields as high as 86% can be obtained depending on the conditions used. In contrast, a yield of only 18% was achieved in the corresponding reaction for the preparation of Acalabrutinib (1) in WO 2013/010868.

Step (ii) is conducted when $G^1$ in the compound of Formula (5) is halide, corresponding with a compound of Formula (5-B):

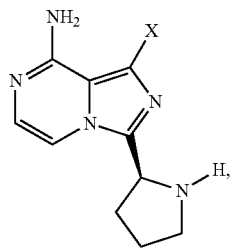

(5-B)

and the product of step (i) is a compound of Formula (2)

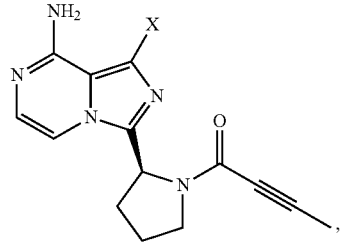

(2)

wherein
X is halide.

The compound of Formula (5) may be obtained from the compound of Formula (6):

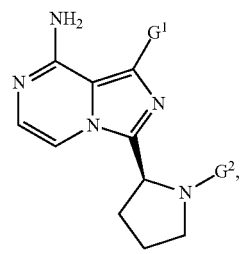

(6)

wherein
$G^1$ is halide or

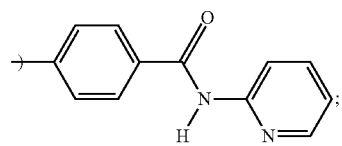

and
$G^2$ is a protecting group.

Compounds of Formula (6) may be prepared by any desired method, including, for example, the processes described in WO 2013/010868 A1.

For example, a compound of Formula (5-A):

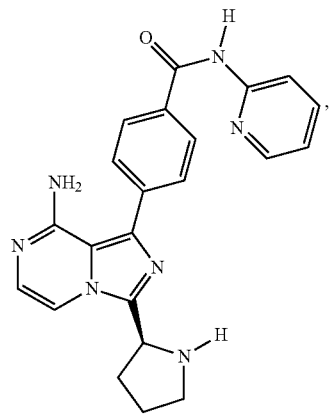

(5-A)

may be obtained by deprotection a compound of Formula (6-A):

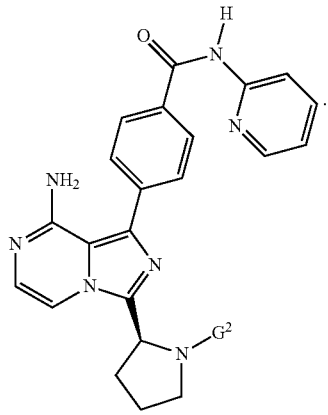

(6-A)

The compound of Formula (6-A) may be prepared using known methods, such as those described in WO 2013/010868, or by a palladium-catalyzed Suzuki-type coupling of the compound of Formula (6-B):

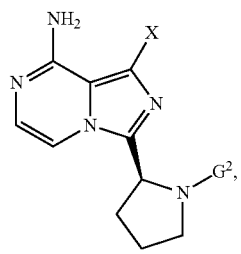

(6-B)

wherein
X is halide; and
$G^2$ is a protecting group;
with a compound of Formula (3), described above, according to the methods described herein for the conversion of the compound of Formula (2) to Acalabrutinib (1) that do not require the use of microwave irradiation.

The compound of Formula (6-B) may be obtained according to methods reported in, for example, WO 2013/010868 A1, utilizing a suitable protecting group $G^2$ to protect the pyrrolidine amine group.

A compound of Formula (5-B) may be obtained by deprotection, that is, removal of protecting group $G^2$, of a compound of Formula (6-B).

In the compounds of Formula (6), $G^2$ is any suitable amine protecting group such as those described in, for example, Greene, T. W.; Wuts, P. G. M. *Protective Groups in Organic Synthesis*; Fourth edition; Wiley: New York, 2007. Preferably, $G^2$ is an alkyloxycarbonyl or an arylalkyloxycarbonyl protecting group such as tert-butyloxycarbonyl (BOC) or benzyloxycarbonyl (Cbz). Preferably, $G^2$ is benzyloxycarbonyl.

In the deprotection of compounds of Formula (6), suitable conditions for cleavage of protecting groups from an amine may be employed. For example, suitable methods may be found in Greene, T. W.; Wuts, P. G. M. *Protective Groups in Organic Synthesis*; Fourth edition; Wiley: New York, 2007.

Preferably, when $G^2$ is a carbamate protecting group, deprotection is conducted by acidolysis or hydrogenolysis (when $G^2$ is arylalkyloxycarbonyl).

Preferably, the deprotection is conducted by acidolysis using a suitable acid. Suitable acids may be selected from the group consisting of trifluoroacetic acid, methanesulfonic acid, p-toluenesulfonic acid, trifluoromethanesulfonic acid, hydrogen chloride, hydrogen bromide, acetic acid and mixtures thereof. Preferably, the acid is a mixture of acetic acid and hydrogen bromide. The suitable acid may also function as solvent for the deprotection. Alternatively, the deprotection may be conducted in the presence of a solvent selected from the group consisting of nitriles, halogenated hydrocarbons and ethers. However, it is preferred that the acid functions as the solvent.

When $G^2$ is arylalkyloxycarbonyl, the deprotection may alternatively be conducted using hydrogenolysis conditions in the presence of a suitable catalyst in a suitable solvent. Preferably, the suitable catalyst is palladium on carbon (Pd/C) or palladium hydroxide on carbon (Pd(OH)$_2$/C), in an amount of between about 0.1 wt % to about 20 wt % with respect to the compound of Formula (6-B). The suitable solvent may be selected from the group consisting of water, alcohols and esters suitable for use in hydrogenation reactions. Preferably, the solvent is methanol.

The deprotection of a compound of Formula (6) may be conducted at any suitable temperature. Preferably, the temperature is in the range of about 15° C. to about 35° C.

In the compound of Formula (3) used in step (ii), $R^1$ and $R^2$ are either (a) two independent groups selected from the group consisting of H and alkyl; or (b) $R^1$ and $R^2$ together form a heterocyclic ring with the boron and oxygen atoms to which they are bonded. When $R^1$ and $R^2$ are both H, the compound of Formula (3) is a boronic acid. Preferably, $R^1$ and $R^2$ together form a heterocyclic ring selected from 4,4,5,5-tetramethyl-1,3,2-dioxaborolanyl (pinacolborane) and 1,3,2-benzodioxaborole (catecholborane).

In the coupling of the compound of Formula (2) and the compound of Formula (3) in step (ii), the palladium catalyst may be any catalyst suitable for Suzuki type coupling reactions. For example, the palladium catalyst may be selected from the group consisting of 1,1'-bis(diphenylphosphino)ferrocene]dichloropalladium (II) (Pd(dppf)Cl$_2$), tetrakis(triphenylphosphine)palladium(0) (Pd(PPh$_3$)$_4$), palladium (II) acetate (Pd(OAc)$_2$), palladium(II) chloride (PdCl$_2$), bis(benzonitrile)palladium(II) dichloride (Pd(PhCN)$_2$Cl$_2$, bis(triphenylphosphine)palladium(II) dichloride (Pd(PPh$_3$)$_2$Cl$_2$), and allylpalladium(II) chloride dimer (PdCl(C$_3$H$_5$)]$_2$). Preferably, the palladium catalyst is 1,1'-bis(diphenylphosphino)ferrocene]dichloropalladium (II) (Pd(dppf)Cl$_2$).

In the coupling of the compound of Formula (2) and the compound of Formula (3) in step (ii), suitable bases (B1) include, for example, tertiary amines, metal carbonates, metal hydroxides and phosphates. For example, base (B1) may be selected from the group consisting of triethylamine, cesium carbonate, potassium carbonate, sodium hydroxide and potassium phosphate. Preferably, the base (B1) is potassium carbonate.

In the coupling of the compound of Formula (2) and the compound of Formula (3), solvent (S2) may be selected from the group consisting of mixtures of water and high boiling (boiling point greater than about 100° C.) ethers such as anisole and 1,4-dioxane. Preferably, solvent (S2) is a mixture of water and 1,4-dioxane.

EXAMPLES

The following examples are illustrative of some of the embodiments of the invention described herein. It will be apparent to the person skilled in the art that various alterations to the described processes in respect of the reactants, reagents and conditions may be made when using the processes of the present invention without departing from the scope or intent thereof.

Example 1: Preparation of Acalabrutinib (1) Using DCC (Carbodiimide) and HOSu (Additive)

a. Preparation of benzyl (2S)-2-(8-amino-1-{4-[(pyridin-2-yl)carbamoyl]phenyl}imidazo[1,5-a]pyrazin-3-yl)pyrrolidine-1-carboxylate (Compound of Formula (6-A1))

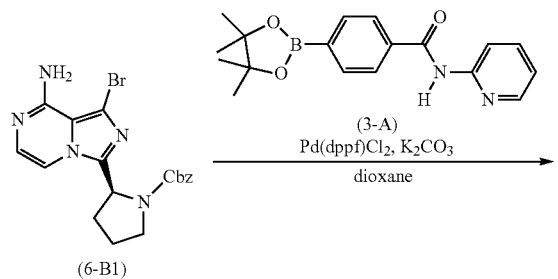

A flask was charged with the compound of Formula (6-B1) (4.00 g, 9.61 mmol) and the compound of Formula (3-A) (3.43 g, 10.57 mmol), 2 N aqueous potassium carbonate solution (48 mL, 96.09 mmol), and 1,4-dioxane (120 mL) to provide a clear, light brown solution at room temperature. The solution was degassed with nitrogen for 2 minutes prior to addition of [1,1'-bis(diphenylphosphino)ferrocene]dichloropalladium(II) (1.76 g, 2.40 mmol). The reaction mixture was heated to reflux at 87° C. After 45 minutes of stirring at reflux, the reaction was deemed complete by TLC (aqueous work up of aliquot into ethyl acetate, TLC solvent system: 1:9 methanol:ethyl acetate, Formula (6-B1) rf=0.46, Formula (6-A1) rf=0.28), and was then cooled to room temperature. Once the reaction mixture was at room temperature, water (160 mL) and ethyl acetate (160 mL) were charged to the flask. The solution was then filtered through polypropylene filter material to remove any emulsion and aid in separation. The filter funnel was washed with ethyl acetate (20 mL). The filtrate was separated and the aqueous phase was further extracted with ethyl acetate (160 mL). The organic phases were combined and washed with brine (160 mL). The organic layer was then separated, dried over anhydrous sodium sulfate, and concentrated in vacuo at 30-35° C. to afford a dark yellow residue (7.8 g). The residue was then purified by column chromatography using ethyl acetate and methanol to afford the compound of Formula (6-A1) as a dark yellow solid (4.56 g, 8.55 mmol, 89% yield).

$^1$H-NMR (CDCl$_3$, 300 MHz) δ: 2.05 (2H, s), 2.23-2.60 (3H, m), 3.60-3.84 (2H, m), 4.77-5.37 (5H, m), 6.86-6.98 (1H, m), 7.06-7.24 (3H, m), 7.34 (2H, s), 7.68-7.87 (4H, m), 8.04 (2H, d, J=8.3 Hz), 8.33 (1H, d, J=4.0 Hz), 8.42 (1H, d, J=8.4 Hz), 8.73 (1H, s).

b. Preparation of 4-{8-amino-3-[(2S)-pyrrolidin-2-yl]imidazo[1,5-a]pyrazin-1-yl}-N-(pyridin-2-yl)benzamide (Compound of Formula (5-A))

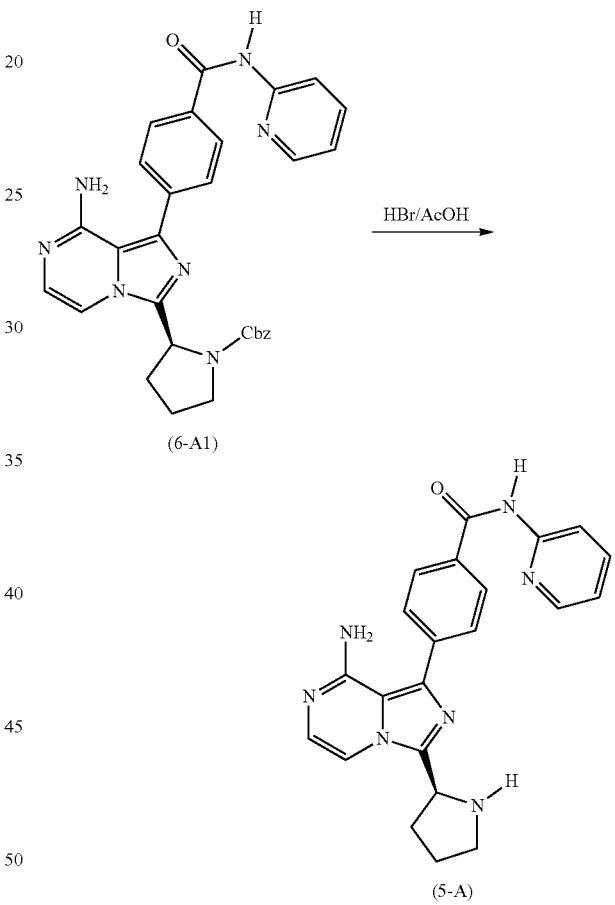

The compound of Formula (6-A1) (4.50 g, 8.43 mmol) was combined with a 33 wt % solution of hydrobromic acid in acetic acid (117 mL, 649.37 mmol) to provide a clear, yellow solution. The consumption of the starting material was observed after 1 hour by TLC (aqueous work up of aliquot basified to pH of 9 with NaOH extracted into dichloromethane, TLC solvent system: 1.5:8.5 methanol:ethyl acetate, Formula (6-A1) rf=0.40, Formula (5-A) rf=0.02). Dichloromethane (160 mL) and water (160 mL) were charged to the flask and stirring was continued at room temperature for 15 minutes before the mixture was transferred to a separatory funnel. The aqueous phase was transferred to a new flask and then basified to a pH of approximately 9 using 2 N aqueous NaOH (1.5 L, 3000 mmol). The aqueous phase was then extracted with dichloromethane (500 mL, 250 mL). The organic phases were combined, dried over anhydrous sodium sulfate, and concentrated in vacuo at 30-35° C. to afford the compound of Formula (5-A) as a yellow solid (2.89 g, 7.22 mmol, 86% yield).

$^1$H-NMR (CDCl$_3$, 300 MHz) δ: 1.85-2.10 (3H, m), 2.15-2.34 (2H, m), 3.04 (1H, ddd, J=6.8 Hz, 7.6 Hz, 10.7 Hz), 3.25 (1H, ddd, J=5.7 Hz, 7.3 Hz, 10.7 Hz), 4.57 (1H, t, J=7.5 Hz), 5.09 (2H, s), 7.08-7.14 (2H, m), 7.59 (1H, d, J=5.0 Hz), 7.75-7.80 (1H, m), 7.80-7.86 (2H, m), 8.02-8.08 (2H, m), 8.34 (1H, ddd, J=0.8 Hz, 1.8 Hz, 4.9 Hz), 8.4 (1H, d, J=8.4 Hz), 8.67 (1H, s).

c. Preparation of 1-[(but-2-ynoyl)oxy]pyrrolidine-2,5-dione (Compound of Formula (4-A))

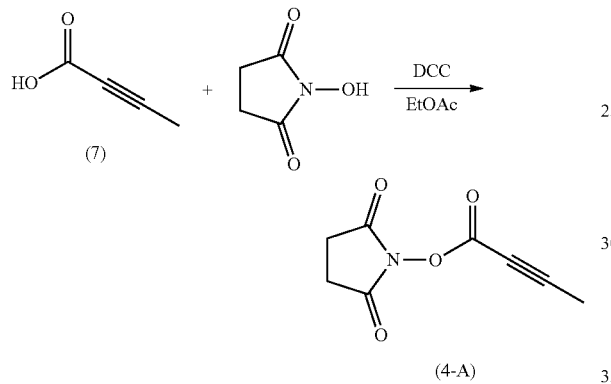

To a solution of 2-butynoic acid (7) (2.00 g, 23.79 mmol) in ethyl acetate (13 mL) was added N-hydroxysuccinimide (2.61 g, 22.66 mmol) and the resulting suspension was cooled to −15 to −10° C. A solution of DCC (4.68 g, 22.66 mmol) in ethyl acetate (8 mL) was prepared and added dropwise to the reaction suspension over a period of 30 minutes. The resulting thick suspension was warmed to 0-5° C. followed by the addition of CELITE® (0.14 g). After a period of 3.5 hours at 0-5° C., the suspension was filtered to remove the CELITE® and the precipitated DCU (1,3-dicyclohexylurea) by-product. The cake was washed with ethyl acetate (3×26 mL) and the filtrate was concentrated in vacuo at 30-35° C. to afford a yellow oil residue (4.98 g) of crude product. This residue (4.98 g) was combined with crude product (1.10 g) obtained from an analogous experiment performed using 0.5 g of the compound of Formula (7). The combined crude material was combined with ethyl acetate (30 mL) and heptanes (70 mL) and stirred at room temperature for 16 hours. The resulting thin suspension was then filtered to remove any further precipitated DCU, and the filtrate was concentrated in vacuo at 30-35° C. to dryness. The resulting residue from the filtrate was then pulped in diethyl ether (75 mL) for 20 minutes and the product was collected by filtration to afford the compound of Formula (4-A) as a white solid (3.56 g, 19.65 mmol, 70% yield).

$^1$H-NMR (CDCl3, 300 MHz) δ: 2.11 (3H, s), 2.85 (4H, s).

d. Preparation of Acalabrutinib (1)

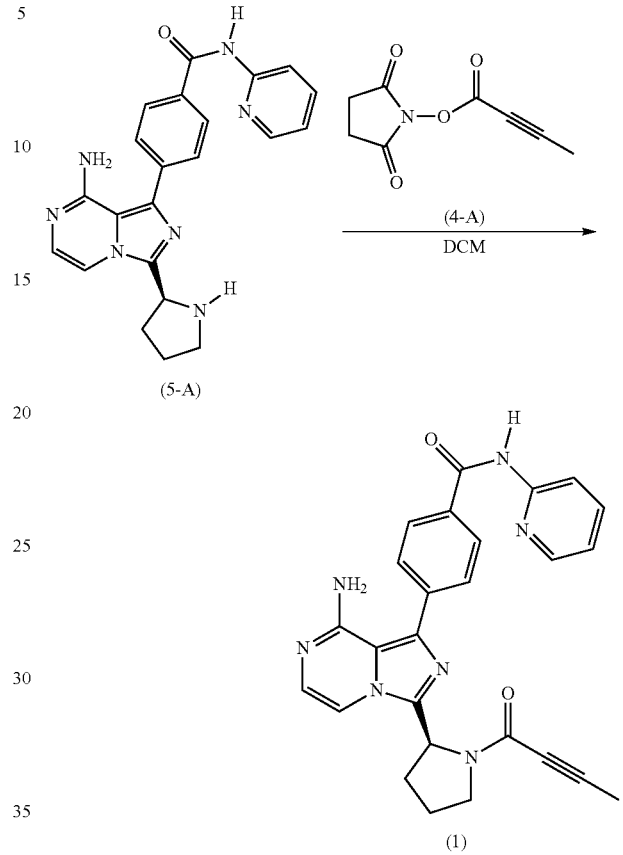

A thick suspension of the compound of Formula (5-A) (2.00 g, 4.99 mmol) in dichloromethane (40 mL) was cooled to 0-5° C. A solution of the compound of Formula (4-A) (0.90 g, 4.99 mmol) in dichloromethane (20 mL) was added to the suspension over 30 minutes. A clear, yellow solution resulted and stirring was continued at 0-5° C. for 25 minutes when the reaction was deemed complete by TLC (aqueous work up of aliquot into dichloromethane, TLC solvent system: 3:7 methanol:ethyl acetate, Formula (5-A) rf=0.05, Formula (1) rf=0.45) and was allowed to warm to room temperature. The reaction solution was then washed with water (40 mL) and the organic layer was then separated, dried over anhydrous sodium sulfate, and concentrated in vacuo at 30-35° C. to afford a yellow solid (2.49 g). The solid was then purified by column chromatography using ethyl acetate and methanol to afford Acalabrutinib (1) as a yellow solid (1.99 g, 4.27 mmol, 86% yield).

$^1$H-NMR (DMSO-d$_6$, 300 MHz; rotamers) δ: 1.62 and 2.01 (3H, s (combined peaks)), 2.08-2.17 (1H, m), 2.18-2.42 (2H, m), 3.31 (1H, s), 3.51-3.69 (1H, m), 3.82 (1H, t, J=6.5 Hz), 5.45-5.32 and 5.67-5.77 (1H, each m), 6.14 and 6.20 (2H, each s), 7.14 (1H, dd, J=4.9 Hz, 11.8 Hz), 7.18 (1H, ddd, J=0.9 Hz, 4.9 Hz, 7.32 Hz), 7.77-7.90 (4H, m), 8.16 (2H, dd, J=1.9 Hz, 8.37 Hz), 8.22 (1H, d, J=8.4 Hz), 8.41 (1H, m), 10.85 (1H, s).

Example 2: Preparation of Acalabrutinib (1) Using DCC (Carbodiimide) and HOSu (Additive) without Isolation of Activated Acid Derivative (4-A)

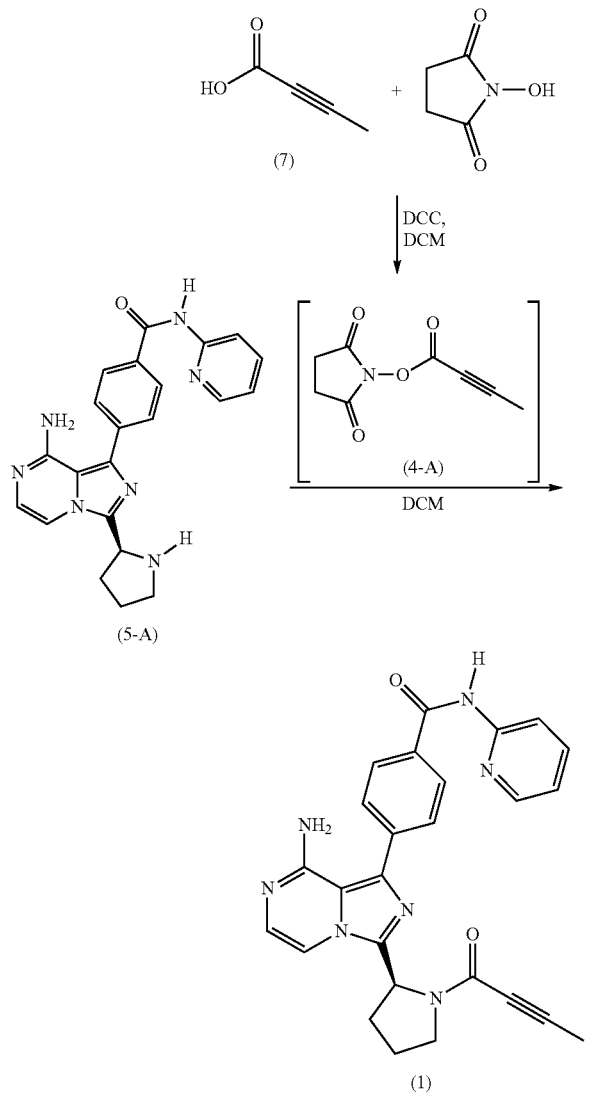

A clear solution of 2-butynoic acid (7) (44 mg, 0.52 mmol) and N-hydroxysuccinimide (57 mg. 0.52 mmol) in dichloromethane (2 mL) was cooled to −15 to −10° C. A solution of DCC (103 mg, 0.50 mmol) in dichloromethane (1 mL) was added dropwise to the reaction solution over 10 minutes forming a white suspension. The reaction was then warmed to 0-5° C. and stirred for 2 hours, at which point it was deemed complete by TLC (6:4 ethyl acetate:heptanes, N-hydroxysuccinimide rf=0.05, Formula (4-A) rf=0.54). The suspension was filtered to remove the precipitated DCU by-product and the cake was washed with dichloromethane (2×1 mL). A $^1$H-NMR (CDCl$_3$) assay of the filtrate using 1,4-dimethoxybenzene as an internal standard was used to estimate the amount of the compound of Formula (4-A) as 74 mg (0.41 mmol).

A suspension of the compound of Formula (5-A) (0.16 g, 0.41 mmol) in dichloromethane (4 mL) was cooled to 0-5° C. The filtrate (6.66 g) containing the compound of Formula (4-A) (74 mg, 0.41 mmol) was added over a period of 10 minutes, which resulted in a clear, yellow solution. The reaction was deemed complete after 1.4 hours by TLC (aqueous work up of aliquot into dichloromethane, TLC solvent system: 2:8 methanol:ethyl acetate, Formula (5-A) rf=0.02, Formula (1) rf=0.30) and was allowed to warm to room temperature. The reaction solution was then washed with water (4 mL) and the organic layer was then separated, dried over anhydrous sodium sulfate, and concentrated in vacuo at 30-35° C. to afford a yellow solid (0.23 g). The solid was then purified by column chromatography using ethyl acetate and methanol to afford Acalabrutinib (1) as a yellow solid (0.13 g, 0.28 mmol, 70% yield).

Example 3: Preparation of Acalabrutinib (1) Using DCC (Carbodiimide) and HOSu (Additive)

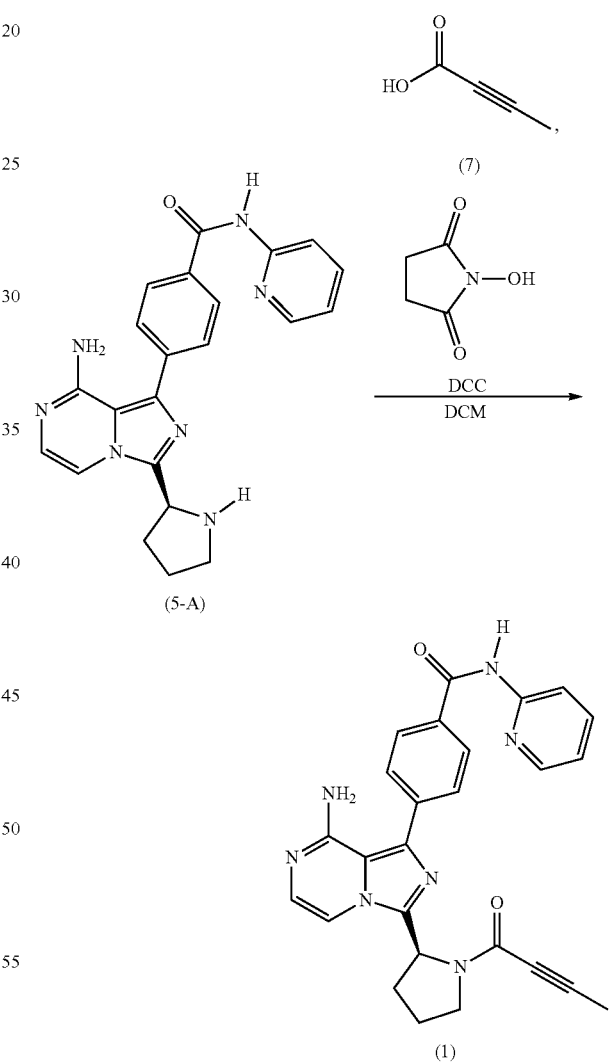

A clear, yellow solution of 2-butynoic acid (7) (42 mg, 0.50 mmol), N-hydroxysuccinimide (58 mg, 0.50 mmol) and the compound of Formula (5-A) (200 mg, 0.50 mmol) in dichloromethane (6 mL) was cooled to −15 to −10° C. A solution of DCC (103 mg, 0.50 mmol) in dichloromethane (1 mL) was added dropwise to the reaction solution over a period of 15 minutes followed by warming the solution to 0-5° C. A slight suspension was formed after a period of 1 hour. The reaction was deemed complete after 2 hours by $^1$H-NMR (consumption of the compound of Formula (5-A)). The reaction suspension was warmed to room temperature and filtered to remove the DCU by-product. The cake was washed with dichloromethane (2×2 mL) and the filtrate was washed with water (1×3 mL). The organic layer was then separated, dried over anhydrous sodium sulfate, and concentrated in vacuo at 30-35° C. to afford a crude product as a yellow solid (0.31 g). The solid was then purified by column chromatography using ethyl acetate and methanol to afford Acalabrutinib (1) as a yellow solid (0.17 g, 0.36 mmol, 72% yield).

Example 4: Preparation of Acalabrutinib (1) Using DCC (Carbodiimide) without Additive

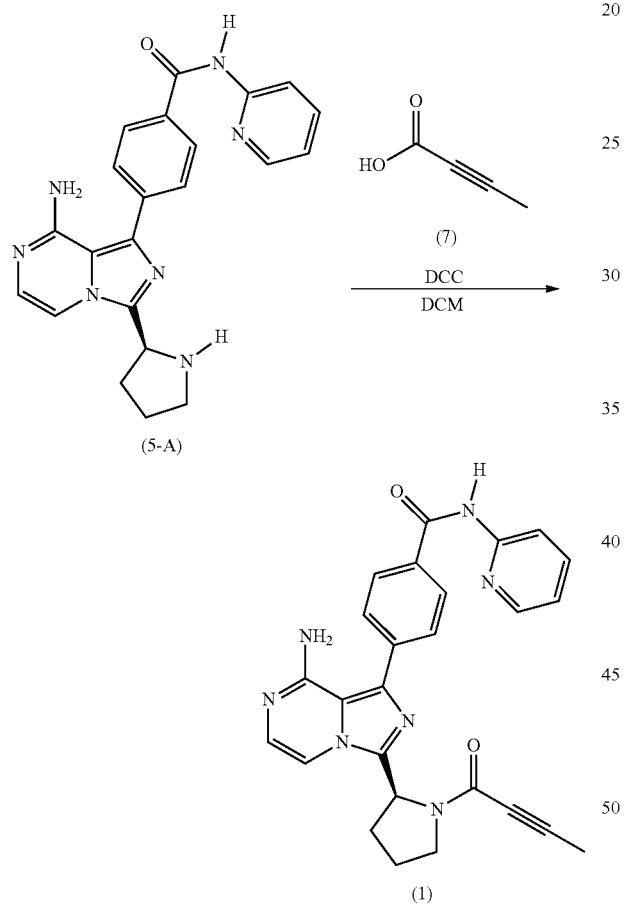

A clear, yellow solution of 2-butynoic acid (7) (25 mg, 0.30 mmol), and the compound of Formula (5-A) (100 mg, 0.25 mmol) in dichloromethane (2 mL) was cooled to −15 to −10° C. A solution of DCC (62 mg, 0.30 mmol) in dichloromethane (1 mL) was added dropwise to the reaction solution over 5 minutes followed by warming to 0-5° C. A slight suspension was formed after a period of 45 minutes. The reaction was deemed complete after 1 hour by TLC (aqueous work up of aliquot into dichloromethane, TLC solvent system: 3:7 methanol:ethyl acetate with KMnO$_4$ stain, Formula (5-A) rf=0.06, Formula (7) rf=0.31, Formula (1) rf=0.47). The reaction suspension was warmed to room temperature and filtered to remove the DCU (1,3-dicyclohexylurea) by-product. The cake was washed with dichloromethane (2×1 mL) and the filtrate was washed with water (2 mL). The organic layer was then separated, dried over anhydrous sodium sulfate, and concentrated in vacuo at 30-35° C. to afford crude Acalabrutinib (1) as a yellow solid (0.12 g).

Example 5: Preparation of Acalabrutinib (1) Using EDC (Carbodiimide) and HOSu (Additive)

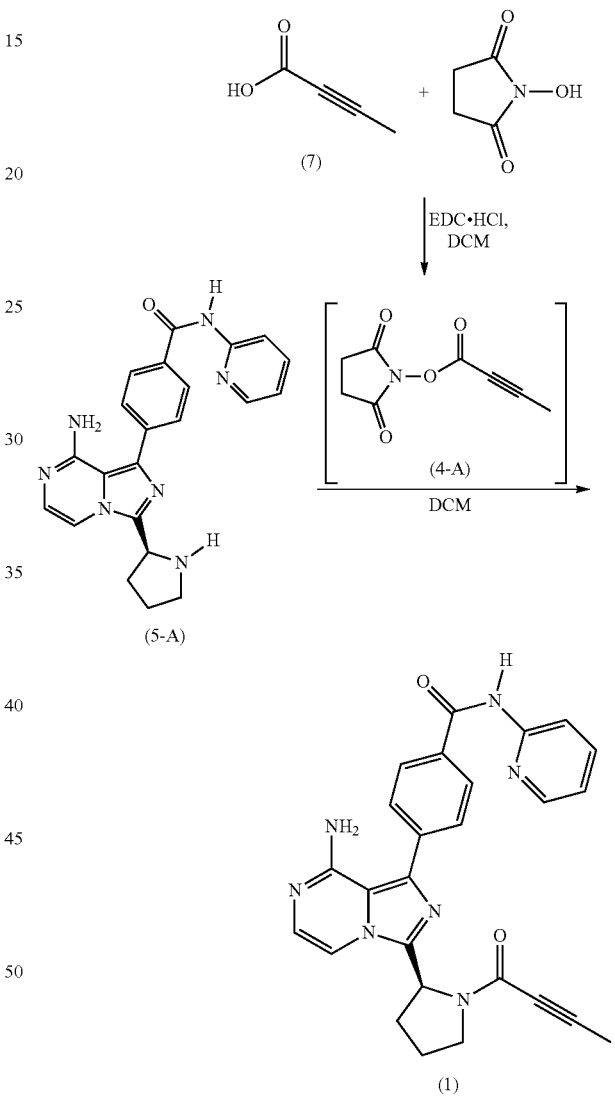

A mixture of 2-butynoic acid (7) (50 mg, 0.60 mmol), N-hydroxysuccinimide (69 mg, 0.60 mmol) and dichloromethane (2 mL) was cooled to −15 to −10° C. yielding a slight suspension. A solution of EDC. HCl (115 mg, 0.60 mmol) in dichloromethane (1 mL) was added dropwise to the reaction suspension over 10 minutes to form a clear, yellow solution. After 1.5 hours, a second portion of EDC. HCl (48 mg, 0.25 mmol) was charged to the reaction solution. The reaction was deemed complete after a total of 2 hours as seen by $^1$H-NMR (complete consumption of the 2-butynoic acid).

This reaction mixture was added dropwise over 10 minutes to a suspension of the compound of Formula (5-A) (0.20 g, 0.50 mmol) in dichloromethane (3 mL) at 0-5° C. whereupon a clear, yellow solution was obtained. The reaction was deemed complete after 10 minutes by TLC (aqueous work up into dichloromethane, 3:7 methanol:ethyl acetate, Formula (5-A) rf=0.06, Formula (1) rf=0.49) and was allowed to warm to room temperature. The reaction solution was then washed with water (3 mL) and the organic layer was then separated, dried over anhydrous sodium sulfate, and concentrated in vacuo at 30-35° C. to afford a yellow solid (0.28 g). The solid was then purified by column chromatography using ethyl acetate and methanol to afford Acalabrutinib (1) as a yellow solid (0.16 g, 0.34 mmol, 69% yield).

Example 6: Preparation of Acalabrutinib (1) Using EDC (Carbodiimide) without Additive

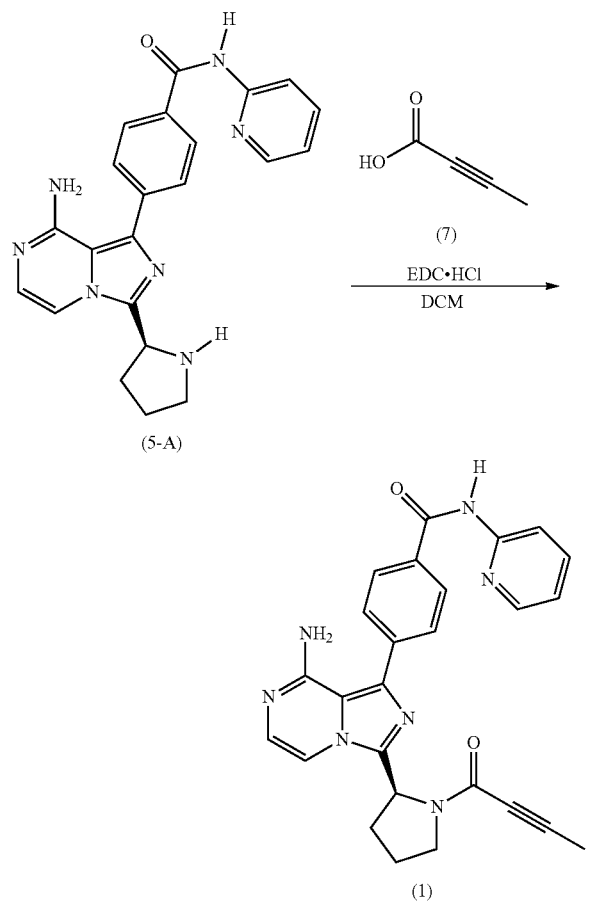

A clear, yellow solution of 2-butynoic acid (25 mg, 0.30 mmol) and the compound of Formula (5-A) (100 mg, 0.25 mmol) in dichloromethane (2 mL) was cooled to −15 to −10° C. A solution of EDC.HCl (58 mg, 0.30 mmol) in dichloromethane (1 mL) was added dropwise to the reaction solution over a period of 5 minutes and then warmed to 0-5° C. The reaction was deemed complete after 45 minutes by TLC (aqueous work up of aliquot into dichloromethane, TLC solvent system: 3:7 methanol:ethyl acetate with KMnO$_4$ stain, Formula (5-A) Intermediate rf=0.06, Formula (7) rf=0.31, Formula (1) rf=0.47) and was warmed to room temperature. The reaction solution was washed with water (2×2 mL) and the organic layer was then separated, dried over anhydrous sodium sulfate, and concentrated in vacuo at 30-35° C. to afford crude Acalabrutinib (1) as a yellow solid (0.11 g). Estimated HPLC purity (area %)=97.2% a/a.

Example 7: Preparation of Acalabrutinib (1) Using DCC (Carbodiimide) and 4-Nitrophenol (Additive)

a. Preparation of 4-nitrophenyl but-2-ynoate (Compound of Formula (4-B))

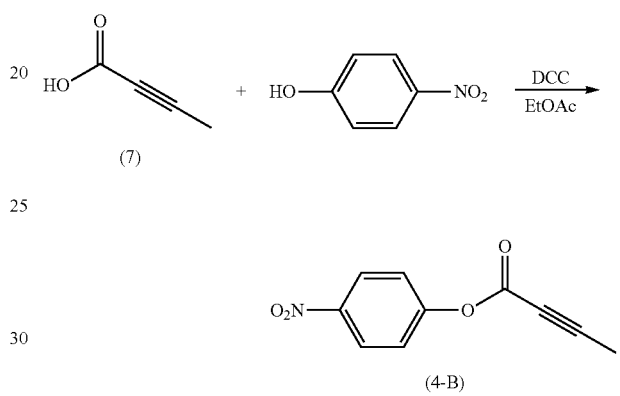

A clear solution of 2-butynoic acid (7) (0.2 g, 2.38 mmol) and 4-nitrophenol (0.32 g, 2.26 mmol) in ethyl acetate (1.5 mL) was cooled to −15 to −10° C. A solution of DCC (0.47 g, 2.26 mmol) in ethyl acetate (0.9 mL) was added dropwise to the reaction suspension over a period of 20 minutes. The resulting thick suspension was warmed to 0-5° C. and stirred at this temperature for 6 hours prior to warming to room temperature and continuing stirring for a further 17 hours. The reaction was monitored by TLC (7:3 heptanes:ethyl acetate with KMnO$_4$ stain, 4-nitrophenol rf=0.35, Formula (4-B) rf=0.50) and with starting material still visible, an additional portion of N,N'-dicyclohexylcarbodiimide (95 mg, 0.46 mmol) was added to the reaction mixture. After 3.5 hours, the reaction was deemed complete by TLC and the suspension was filtered and the cake (DCU by-product) was washed with ethyl acetate (0.5 mL). The filtrate was concentrated in vacuo at 30-35° C. to dryness to afford a white solid residue (0.60 g). $^1$H-NMR determined that the residue was a mixture of the target product and unreacted N,N'-dicyclohexylcarbodiimide. The residue (0.60 g) was pulped in heptanes (15 mL) and ethyl acetate (0.1 mL) at room temperature for 45 minutes. The suspension was then filtered and the cake washed with heptanes (2 mL) to afford the compound of Formula (4-B) as a white solid (0.33 g, 1.61 mmol, 70% yield).

$^1$H-NMR (CDCl$_3$, 300 MHz) δ: 2.10 (3H, s), 7.34 (2H, AA'XX', J$_{AA'}$=7.3 Hz, J$_{XX'}$=1.9 Hz, J$_{AX}$=8.9 Hz, J$_{AX'}$=0.3 Hz), 8.29 (2H, AA'XX', J$_{AA'}$=7.2 Hz, J$_{XX'}$=1.9 Hz, J$_{AX}$=8.9 Hz, J$_{AX'}$=0.3 Hz).

b. Preparation of Acalabrutinib (1)

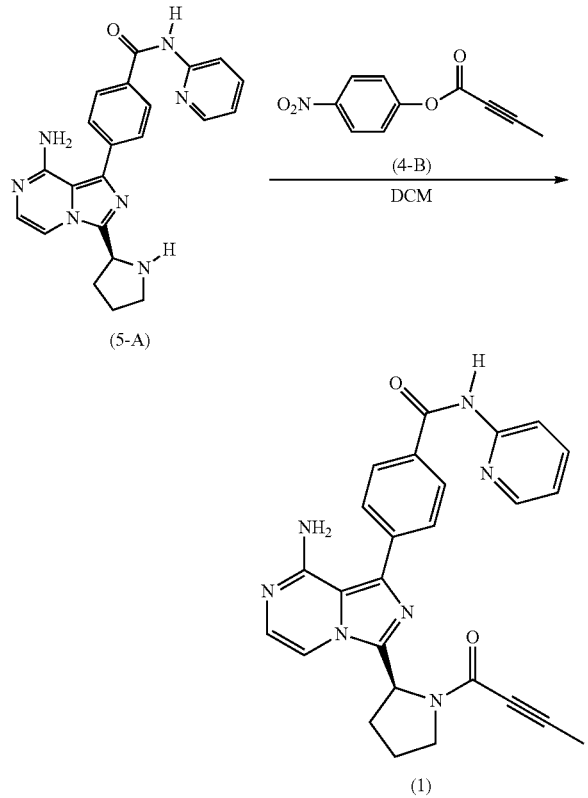

A thick suspension of the compound of Formula (5-A) (0.20 g, 0.50 mmol) in dichloromethane (4 mL) was cooled to 0-5° C. A solution of the compound of Formula (4-B) (0.10 g, 0.50 mmol) in dichloromethane (2 mL) and was added to the reaction suspension over 30 minutes. The resulting thin suspension was stirred at 0-5° C. The reaction was deemed complete after 1.5 hours by TLC (aqueous work up of aliquot into dichloromethane, TLC solvent system: 3:7 methanol:ethyl acetate, Formula (5-A) rf=0.05, Formula (1)=0.41) and was allowed to warm to room temperature. The reaction solution was then washed with water (4 mL) and the organic layer was then separated, dried over anhydrous sodium sulfate, and concentrated in vacuo at 30-35° C. to afford a yellow solid (0.25 g). The solid was purified by column chromatography using ethyl acetate and methanol to afford Acalabrutinib (1) as a yellow solid (0.17 g, 0.36 mmol, 73% yield).

Example 8: Preparation of Acalabrutinib (1) Using DCC (Carbodiimide) and HOBt (Additive)

a. Preparation of 1-[(but-2-ynoyl)oxy]-1H-benzotriazole (Compound of Formula (4-C))

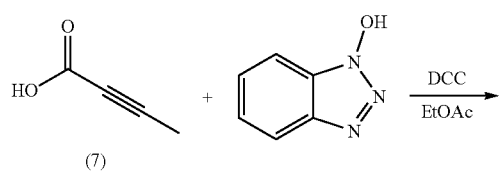

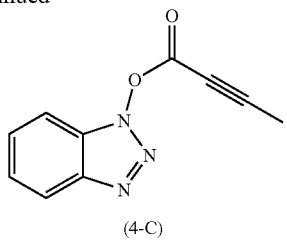

A suspension of 2-butynoic acid (7) (0.2 g, 2.38 mmol) and 1-hydroxy-1H-benzotriazole (0.31 g, 2.26 mmol) in ethyl acetate (1.5 mL) was cooled to −15 to −10° C. A solution of DCC (0.47 g, 2.26 mmol) in ethyl acetate (0.9 mL) was added dropwise to the reaction suspension over a period of 20 minutes and the resulting thick suspension was warmed to 0-5° C. The reaction was monitored by TLC and was deemed complete after 4 hours. The suspension was filtered and the cake (DCU by-product) was washed with cold (0-5° C.) ethyl acetate (0.5 mL). The filtrate was concentrated in vacuo at 30-35° C. to dryness to afford 1-[(but-2-ynoyl)oxy]-1H-benzotriazole (0.41 g, 2.04 mmol, 88% yield) as an off-white solid.

$^1$H-NMR (CDCl$_3$, 300 MHz) δ: 2.22 (3H, s), 7.60 (1H, apparent t, J=7.8 Hz), 7.80 (1H, apparent t, J=7.8 Hz), 8.02 (1H, d, J=8.4 Hz), 8.38 (1H, d, J=8.4 Hz).

b. Preparation of Acalabrutinib (1)

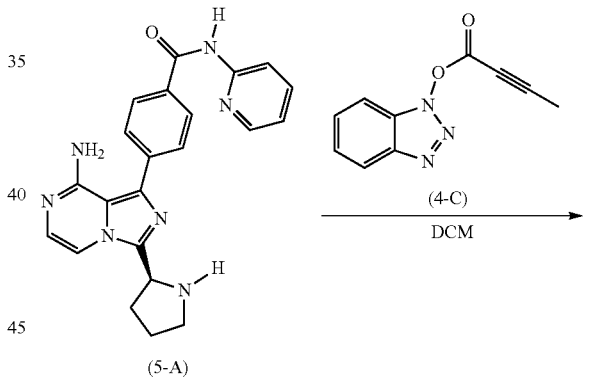

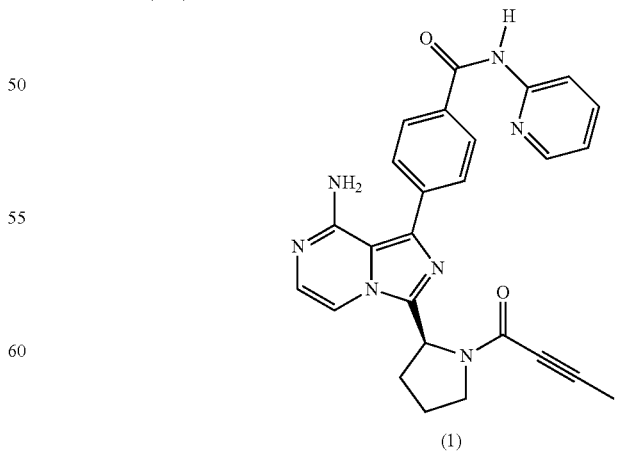

A thick suspension of the compound of Formula (5-A) (0.20 g, 0.50 mmol) in dichloromethane (4 mL) was cooled to 0-5° C. A solution of the compound of Formula (4-C) (0.10 g, 0.50 mmol) in dichloromethane (2 mL) was added to the reaction suspension over 30 minutes and the resulting clear, light yellow solution was stirred at 0-5° C. The reaction was deemed complete after 45 minutes by TLC (aqueous work up of aliquot into dichloromethane, TLC solvent system: 3:7 methanol:ethyl acetate Formula (5-A) rf=0.05, Formula (1) rf=0.41) and was allowed to warm to room temperature. The reaction solution was then washed with water (4 mL) and the organic layer was then separated, dried over anhydrous sodium sulfate, and concentrated in vacuo at 30-35° C. to afford a yellow solid (0.24 g). The solid was purified by column chromatography using ethyl acetate and methanol to afford Acalabrutinib (1) as a yellow solid (0.16 g, 0.34 mmol, 70% yield).

Example 9: Preparation of Acalabrutinib (1) Via a Compound of Formula L2)

a. Preparation of 1-bromo-3-[(2S)-pyrrolidin-2-yl]imidazo[1,5-a]pyrazin-8-amine (Compound of Formula (5-B1))

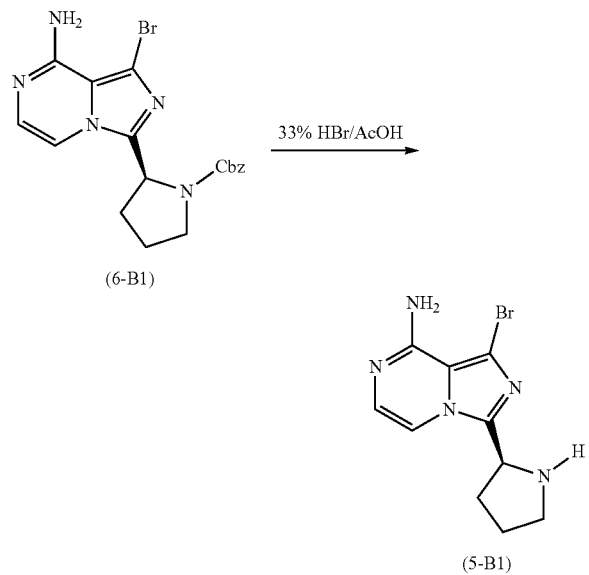

A suspension of the compound of Formula (6-B1) (8.30 g, 15.55 mmol) and hydrobromic acid solution (33 wt % in acetic acid, 46 mL, 254.00 mmol) was stirred at room temperature. The suspension changed to a clear orange solution after 30 minutes of stirring and was deemed complete by TLC (aqueous work up of aliquot basified to pH of 9 with NaOH, extracted into dichloromethane, TLC solvent system: 2:8 methanol:ethyl acetate, Formula (6-B1) rf=0.52, Formula (5-B1) rf=0.05) after 1.5 hours. Water (220 mL) and dichloromethane (220 mL) were charged to the flask and stirring continued at room temperature for 10 minutes. The aqueous phase was transferred to a new flask, cooled to 0-5° C. and then basified to a pH of approximately 9 using 4 N aqueous NaOH (275 mL, 1100 mmol) keeping the internal temperature less than 15° C. The aqueous phase was then extracted with dichloromethane (2×500 mL, 1×250 mL) and the organic phases were combined, dried over anhydrous sodium sulfate, and concentrated in vacuo at 30-35° C. to afford the compound of Formula (5-B1) as an off-white solid (5.62 g, 14.03 mmol, yield=90%).

$^1$H-NMR (CDCl$_3$, 300 MHz) δ: 1.80-2.29 (5H, m), 3.01 (1H, ddd, J=6.6 Hz, 7.6 Hz, 10.7 Hz), 3.18 (1H, ddd, J=5.9 Hz, 7.3 Hz, 10.7 Hz), 4.47 (1H, t, J=7.3 Hz), 4.88-6.13 (2H, broad s), 7.02 (1H, d, J=5.1 Hz), 7.51 (1H, d, J=5.1 Hz).

b. Preparation of 1-[(2S)-2-(8-amino-1-bromoimidazo[1,5-a]pyrazin-3-yl)pyrrolidin-1-yl]but-2-yn-1-one (Compound of Formula (2-A))

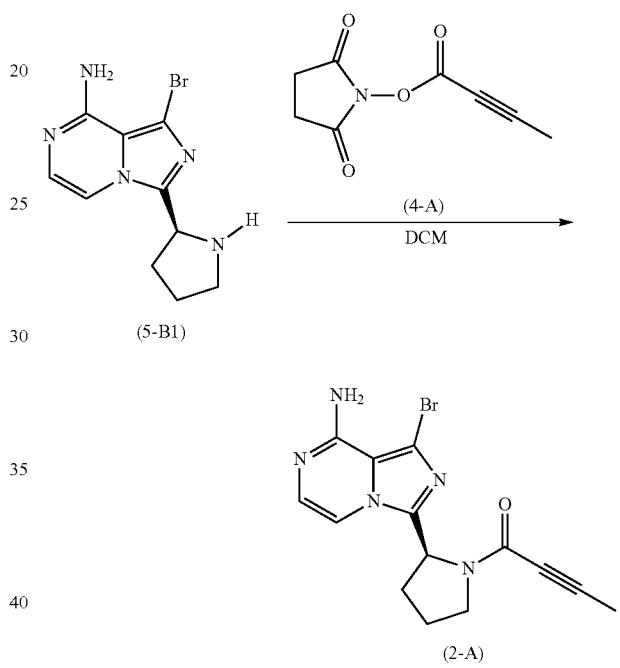

A clear solution of the compound of Formula (5-B1) in dichloromethane (35 mL) was cooled to 0-5° C. A solution of the compound of Formula (4-A) (1.22 g, 6.75 mmol in dichloromethane (17 mL) was added to the reaction solution over 15 minutes. The reaction was deemed complete after 15 minutes by TLC (aqueous work up of aliquot into dichloromethane, TLC solvent system: 2:8 methanol:ethyl acetate, Formula (5-B1) rf=0.05, Formula (2-A) rf=0.34) and was allowed to warm to room temperature. The reaction solution was then washed with water (35 mL) and the organic layer was then separated, dried over anhydrous sodium sulfate, and concentrated in vacuo at 30-35° C. to afford a yellow foamy solid (2.00 g). The solid was purified by column chromatography using ethyl acetate and methanol to afford the compound of Formula (2-A) as a yellow foamy solid (1.83 g, 5.25 mmol, 86% yield).

$^1$H-NMR (CDCl$_3$, 400 MHz) δ: 1.98 (3H, s), 2.00-2.21 (1H, m), 2.24-2.37 (1H, m), 2.38-2.56 (2H, m), 3.71-3.92 (2H, m), 5.30-5.40 (1H, m), 5.50-5.76 (2H, m), 7.06 (1H, m), 7.73 (1H, d, J=5.3 Hz).

c. Preparation of Acalabrutinib (1)

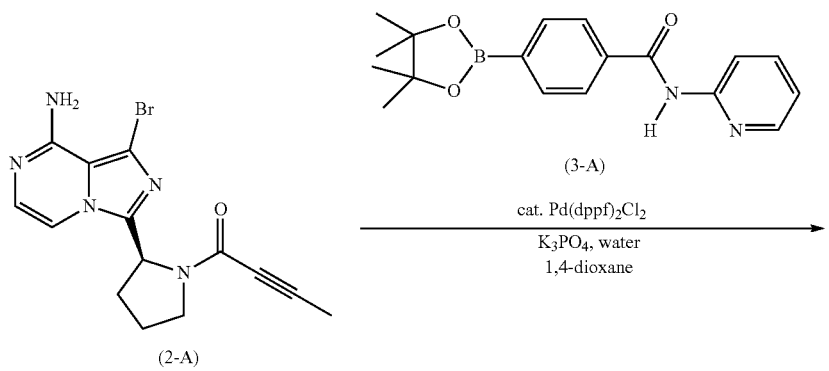

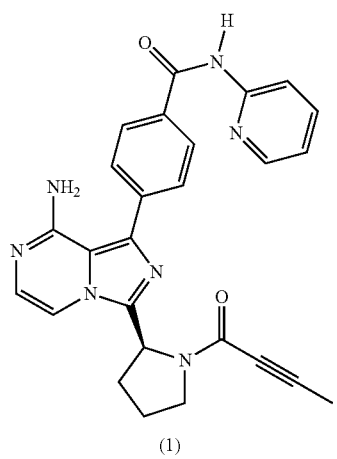

(1)

A clear solution of the compound of Formula (2-A) (0.20 g, 0.57 mmol), the compound of Formula (3-A) (0.21 g, 0.63 mmol), potassium carbonate (0.49 g, 2.29 mmol), water (3 mL), and 1,4-dioxane (6 mL) was degassed with nitrogen for 2 minutes prior to addition of [1,1'-bis(diphenylphosphino)ferrocene]dichloropalladium(II) (105 mg, 0.14 mmol). The reaction mixture was heated to 50° C. After 2 hours of heating the reaction was deemed complete by TLC (aqueous work up of aliquot into ethyl acetate, TLC solvent system: 1.5:8.5 methanol:ethyl acetate, Formula (2-A) rf=0.28, Formula (1) rf=0.20), and was then cooled to room temperature. Water (8 mL) and dichloromethane (8 mL) were charged to the flask. The aqueous phase was then further extracted with dichloromethane (8 mL) and the organic phases were combined, dried over anhydrous sodium sulfate, and concentrated in vacuo at 30-35° C. to afford crude Acalabrutinib (1) as a dark residue (0.36 g).

What is claimed is:
1. A process for the preparation of Acalabrutinib (1):

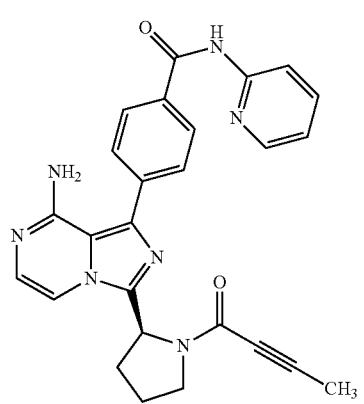

(1)

comprising:
(i) treating a compound of Formula (7):

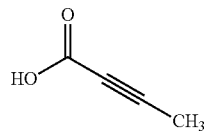
(7)

with a carbodiimide selected from the group consisting of:

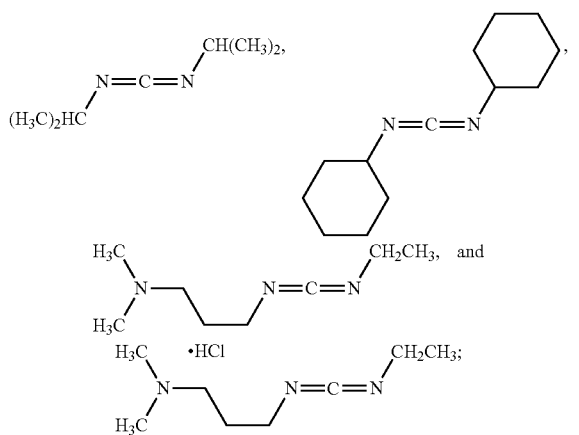

optionally in the presence of Additive (A-H):
A-H,
wherein:
A is selected from the group consisting of:

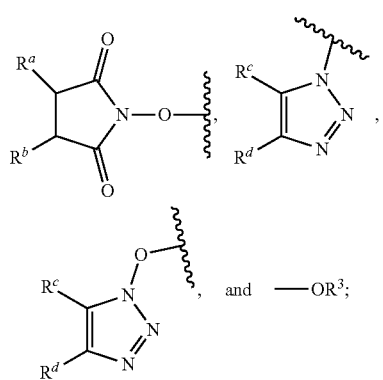

wherein:
(a) $R^a$ is H; and
    $R^b$ is H; or
(b) $R^a$ is $R^c$; and
    $R^b$ is $R^d$;
    $R^c$ and $R^d$, taken together with the carbon atoms to which they are bonded, form a $C_{3-12}$ cycloaliphatic, $C_{6-10}$ aryl, or $C_{5-9}$ heteroaryl, wherein the $C_{3-12}$ cycloaliphatic, $C_{6-10}$ aryl, and $C_{5-9}$ heteroaryl are each optionally substituted with nitro, and further wherein the $C_{5-9}$ heteroaryl has at least one heteroatom selected from the group consisting of nitrogen, oxygen, and sulfur; and
$R^3$ is $C_{6-10}$ aryl, optionally substituted with nitro;

to provide an activated acid derivative selected from the group consisting of (a) and (b):
(a)

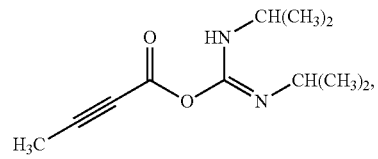

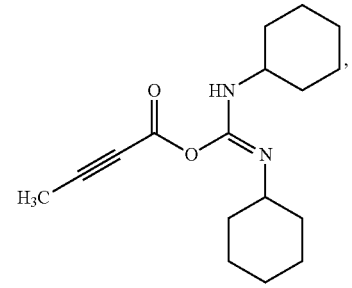

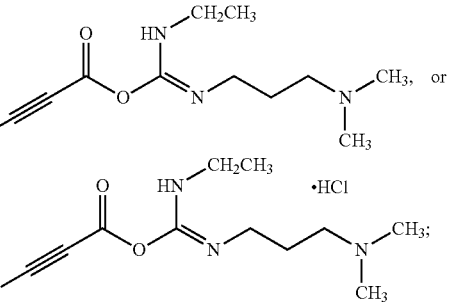

and
(b) a compound of Formula (4):

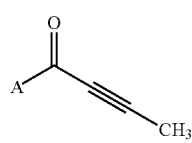
(4)

wherein:
A is selected from the group consisting of:

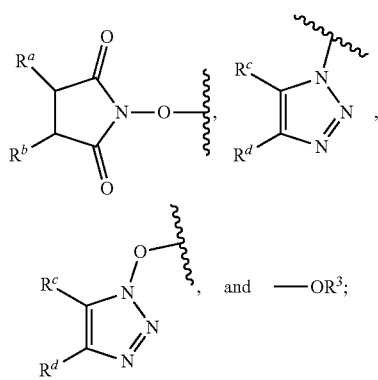

wherein:
(a) $R^a$ is H; and
$R^b$ is H; or
(b) $R^a$ is $R^c$; and
$R^b$ is $R^d$;
$R^c$ and $R^d$, taken together with the carbon atoms to which they are bonded, form a $C_{3-12}$ cycloaliphatic, $C_{6-10}$ aryl, or $C_{5-9}$ heteroaryl, wherein the $C_{3-12}$ cycloaliphatic, $C_{6-10}$ aryl, and $C_{5-9}$ heteroaryl are each optionally substituted with nitro, and further wherein the $C_{5-9}$ heteroaryl has at least one heteroatom selected from the group consisting of nitrogen, oxygen, and sulfur; and
$R^3$ is $C_{6-10}$ aryl, optionally substituted with nitro; and (ii) coupling the activated acid derivative formed in step (i) above with a compound of Formula (5):

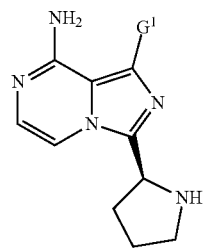

(5)

wherein:
$G^1$ is

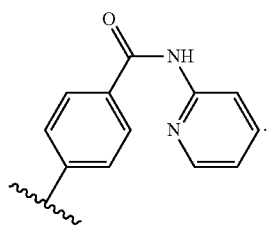 [SMILES: *c1ccc(C(=O)Nc2ccccn2)cc1]

2. The process of claim 1, wherein the carbodiimide is selected from the group consisting of:

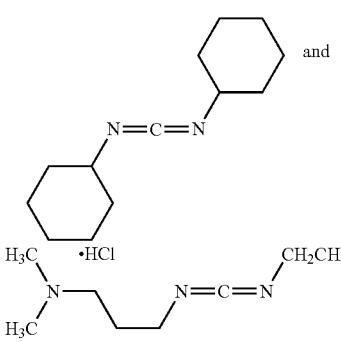

3. The process of claim 1, wherein the compound of Formula (7) is treated with a carbodiimide in the presence of Additive (A-H) to provide the activated acid derivative.

4. The process of claim 3, wherein:
$R^c$ and $R^d$, taken together with the carbon atoms to which they are bonded, form a phenyl, optionally substituted with nitro; and
$R^3$ is phenyl, optionally substituted with nitro.

5. The process of claim 3, wherein Additive (A-H) is selected from the group consisting of:

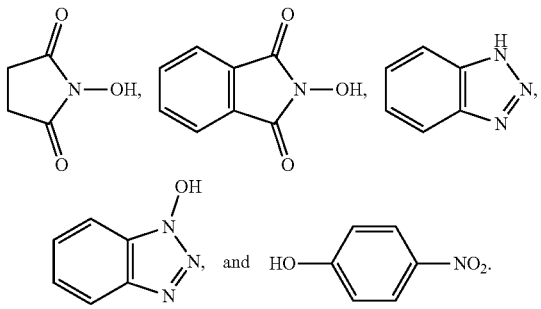

6. The process of claim 3, wherein the activated acid derivative is a compound of Formula (4):

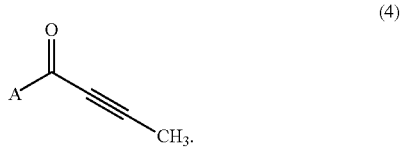

(4)

7. The process of claim 6, wherein A is selected from the group consisting of:

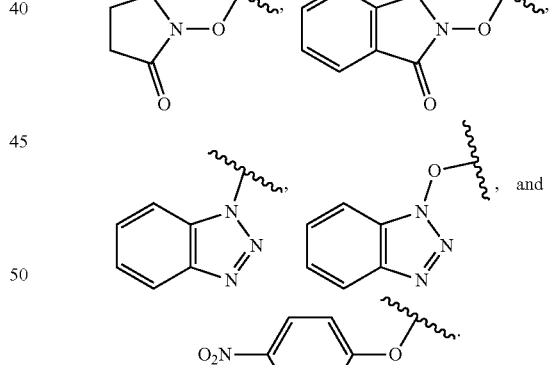

8. The process of claim 6, wherein the activated acid derivative is the compound of Formula (4-A):

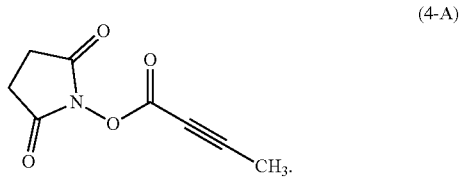 [SMILES: CC#CC(=O)ON1C(=O)CCC1=O]

(4-A)

9. The process of claim 6, wherein the activated acid derivative is isolated prior to step (ii).

10. The process of claim 3, wherein step (i) is completed prior to performing step (ii).

* * * * *